(12) United States Patent
Kim et al.

(10) Patent No.: US 8,889,891 B2
(45) Date of Patent: Nov. 18, 2014

(54) METHOD FOR PREPARING A FURFURANOL-BASED COMPOUND AND 2-FURANCARBOXYLIC ACID-BASED COMPOUND USING AN IONIC LIQUID AS A SOLVENT

(75) Inventors: Baek Jin Kim, Cheonan-si (KR); Jin Ku Cho, Yongin-si (KR); Sangyong Kim, Cheonan-si (KR); Young Gyu Kim, Gunpo-si (KR); Eun-Sil Kang, Seoul (KR); Da Won Chae, Seoul (KR)

(73) Assignees: Korea Institute of Industrial Technology, Chungcheongnam-Do (KR); Seoul National University R&DB Foundation, Seoul (KR)

( * ) Notice: Subject to any disclaimer, the term of this patent is extended or adjusted under 35 U.S.C. 154(b) by 0 days.

(21) Appl. No.: 14/000,500

(22) PCT Filed: Mar. 19, 2012

(86) PCT No.: PCT/KR2012/001914
§ 371 (c)(1),
(2), (4) Date: Sep. 10, 2013

(87) PCT Pub. No.: WO2012/128510
PCT Pub. Date: Sep. 27, 2012

(65) Prior Publication Data
US 2013/0345446 A1    Dec. 26, 2013

(30) Foreign Application Priority Data
Mar. 23, 2011    (KR) ........................ 10-2011-0025675

(51) Int. Cl.
*C07D 307/44*    (2006.01)
*C07D 307/64*    (2006.01)
*C07D 307/68*    (2006.01)

(52) U.S. Cl.
CPC ............ *C07D 307/68* (2013.01); *C07D 307/64* (2013.01); *C07D 307/44* (2013.01)
USPC .......................................... 549/484; 549/502

(58) Field of Classification Search
CPC ... C07D 307/68; C07D 307/64; C07D 307/44
See application file for complete search history.

(56) References Cited

U.S. PATENT DOCUMENTS

| 2008/0033187 A1 | 2/2008 | Zhao et al. |
| 2010/0058650 A1 | 3/2010 | Gruter et al. |
| 2010/0081833 A1 | 4/2010 | Gruter et al. |

OTHER PUBLICATIONS

Kang et al., Journal of Industrial and Engineering Chemistry, 18, 2012, 174-177.*
International Search Report of PCT/KR2012/001914 dated Mar. 19, 2012.

* cited by examiner

*Primary Examiner* — Sun Jae Yoo
(74) *Attorney, Agent, or Firm* — Lucas & Mercanti, LLP

(57) ABSTRACT

This invention relates to a method of, in an eco-friendly manner, preparing a furfuranol-based compound and a 2-furancarboxylic acid-based compound using an ionic liquid as a reaction solvent, which includes reacting a furfural-based compound with a hydroxide of an alkali metal or an alkaline earth metal using an ionic liquid as the solvent, thus obtaining a furfuranol-based compound and a 2-furancarboxylic acid-based compound, and in which water is not used as the reaction solvent, thus preventing the generation of reaction wastewater, and the ionic liquid used as the solvent can be easily recovered and reused.

11 Claims, No Drawings

METHOD FOR PREPARING A FURFURANOL-BASED COMPOUND AND 2-FURANCARBOXYLIC ACID-BASED COMPOUND USING AN IONIC LIQUID AS A SOLVENT

CROSS-REFERENCE TO RELATED APPLICATIONS

This application is a 371 of PCT/KR2012/001914 filed on Mar. 19, 2012, which claims the priority of KR Application Serial No. 10-2011-0025675 filed on Mar. 23, 2011, the contents of each of which are incorporated herein by reference.

TECHNICAL FIELD

The present invention relates to a method of preparing a furfuranol-based compound and a 2-furancarboxylic acid-based compound, and, more particularly, to a method of preparing a furfuranol-based compound and a 2-furancarboxylic acid-based compound using an ionic liquid as a solvent, which is eco-friendly and profitably and exhibits high reaction efficiency.

BACKGROUND ART

Because of the exhaustion of typical sources of energy and the increase in global energy demand, the development of alternative energy is currently receiving attention. In particular, biomass is a renewable quantitative biological resource which is greatly gaining attention as shown in 'Production of Fuel from Biomass' which is the alternative energy development project conducted by the Department of Energy, USA. 5-hydroxymethylfurfural (HMF) is a biomass-derived material, which may be used instead of petrochemical based compounds whose production and use have been already established, and thorough research thereto is ongoing to date.

2,5-dihydroxymethylfuran which is a kind of furfuranol-based compound and 5-hydroxymethylfuranoic acid (HMFA) which is a kind of 2-furancarboxylic acid-based compound may be obtained via simple conversion of functional groups of 5-hydroxymethylfurfural (HMF) which is a kind of furfural-based compound, and are receiving attention as monomers necessary for synthesizing next-generation high performance and eco-friendly materials as replacements of conventional polymer products.

Currently, synthesis methods related to DHMF and HMFA include reactions using hydrogen or oxygen in the presence of a catalyst with the use of typical organic or inorganic oxidant/reductant, but such methods are difficult to commercialize because of a variety of constraints including vigorous reaction conditions such as high temperature and high pressure upon oxidation/reduction. Furthermore, these are problematic because the oxidants/reductants and catalysts used in conventional processes are expensive, and eco-unfriendly products may result due to the use of heavy metals, and also DHMF and HMFA have to be produced using respective independent processes.

Thus, if methods of efficiently preparing the above two materials are developed and mass production processes thereof are also provided, sufficiently inexpensive reactants may be ensured, thereby increasing their demand as industrial products.

DISCLOSURE

Technical Problem

Accordingly, the present invention has been made keeping in mind the above problems occurring in the related art, and a first object of the present invention is to provide a method of, in an eco-friendly manner, preparing a furfuranol-based compound and a 2-furancarboxylic acid-based compound using an ionic liquid as a reaction solvent, in which water is not used as the reaction solvent thus preventing the generation of reaction wastewater and also the ionic liquid used as the solvent may be easily recovered and reused.

A second object of the present invention is to provide a method of profitably preparing a furfuranol-based compound and a 2-furancarboxylic acid-based compound, which has a simple preparation process and a high reaction yield.

A third object of the present invention is to provide a method of preparing a furfuranol-based compound and a 2-furancarboxylic acid-based compound, which may use a biomass-derived material as a reactant.

Technical Solution

In order to accomplish the above objects, the present invention provides a method of preparing a furfuranol-based compound and a 2-furancarboxylic acid-based compound, comprising reacting a furfural-based compound represented by Chemical Formula 1 below with a hydroxide of an alkali metal or an alkaline earth metal using an ionic liquid as a solvent, thus obtaining a furfuranol-based compound represented by Chemical Formula 2 below and a 2-furancarboxylic acid-based compound represented by Chemical Formula 3 below.

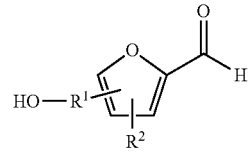

[Chemical Formula 1]

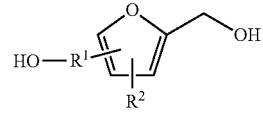

[Chemical Formula 2]

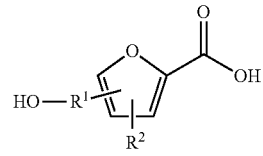

[Chemical Formula 3]

In Chemical Formulas 1 to 3, $R^1$ may be independently a valence bond, a $C_{1-10}$ alkylene group, a $C_{3-14}$ cycloalkylene group, a $C_{6-14}$ arylene group, a $C_{6-14}$ alkylarylene group or a $C_{6-14}$ arylalkylene group, and $R^2$ may be independently a hydrogen atom, a $C_{1-10}$ alkyl group, a $C_{3-14}$ cycloalkyl group, a $C_{6-14}$ aryl group, a $C_{6-14}$ alkylaryl group or a $C_{6-14}$ arylalkyl group.

In Chemical Formulas 1 to 3, $R^1$ may be independently a valence bond or a $C_{1-3}$ alkylene group, and $R^2$ may be independently a hydrogen atom or a $C_{1-3}$ alkyl group.

The method may further comprise, after the reacting, adding a first organic solvent which selectively dissolves the ionic liquid and then performing filtering so that the furfuranol-based compound of Chemical Formula 2 and the 2-furancarboxylic acid-based compound in metal salt form of Chemical Formula 3 are filtered; and subjecting the first organic solvent to fractional distillation to separate the ionic liquid from the first organic solvent which selectively dissolved the ionic liquid.

The method may further comprise, after the filtering, dissolving the furfuranol-based compound of Chemical Formula 2 and the 2-furancarboxylic acid-based compound in metal salt form of Chemical Formula 3, which were filtered, in water to obtain a compound solution, adjusting a pH of the compound solution to 7~8, adding a second organic solvent thereto, and then performing extraction, thus separating the furfuranol-based compound of Chemical Formula 2; and adjusting a pH of the solution from which the furfuranol-based compound of Chemical Formula 2 was extracted to an acidic range, adding a third organic solvent thereto, and then performing extraction, thus separating the 2-furancarboxylic acid-based compound of Chemical Formula 3.

The ionic liquid may be one or more selected from the group consisting of an ammonium salt represented by Chemical Formula 4 below, an ammonium salt or phosphonium salt represented by Chemical Formula 5 below, and a sulfonium salt represented by Chemical Formula 6 below.

[Chemical Formula 4]

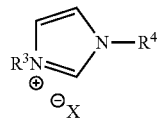

[Chemical Formula 5]

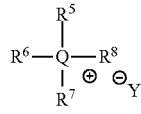

[Chemical Formula 6]

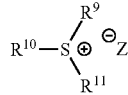

In Chemical Formulas 4 to 6, $R^3$ to $R^{11}$ which are the same as or different from each other may be independently a $C_{1-10}$ linear alkyl group, a $C_{3-10}$ branched alkyl group, or a $C_{5-10}$ cycloalkyl group, the main chain or side chain of the $C_{1-10}$ linear alkyl group, $C_{3-10}$ branched alkyl group, or $C_{5-10}$ cycloalkyl group being unsubstituted or substituted with an oxygen atom, a sulfur atom, a nitrogen atom, a double bond or a triple bond, Q is a nitrogen atom (N) or a phosphorus atom (P), and X, Y and Z which are the same as or different from each other may be independently one or more selected from among $F^-$, $Cl^-$, $Br^-$, $I^-$, $NO_3^-$, $N(CN)_2^-$, $BF_4^-$, $ClO_4^-$, $PF_6^-$, $(CF_3)_2PF_4^-$, $(CF_3)_3PF_3^-$, $(CF_3)_4PF_2^-$, $(CF_3)_5PF^-$, $(CF_3)_6P^-$, $CF_3SO_3^-$, $CF_3CF_2SO_3^-$, $(CF_3SO_2)_2N^-$, $(FSO_2)_2N^-$, $CF_3CF_2(CF_3)_2CO^-$, $(CF_3SO_2)_2CH^-$, $(SF_5)_3C^-$, $(CF_3SO_2)_3C^-$, $CF_3(CF_2)_7SO_3^-$, $CF_3CO_2^-$, $CH_3CO_2^-$, $SCN^-$, and $(CF_3CF_2SO_2)_2N^-$.

The hydroxide of the alkali metal or the alkaline earth metal may be one or more selected from the group consisting of lithium hydroxide, sodium hydroxide, potassium hydroxide, rubidium hydroxide, cesium hydroxide, francium hydroxide, magnesium hydroxide, calcium hydroxide, strontium hydroxide, barium hydroxide and radium hydroxide.

The alkali metal or the alkaline earth metal may be used in an amount of 1~30 parts by equivalent based on 1 part by equivalent of the furfural-based compound represented by Chemical Formula 1.

In the method, reacting may be performed at 0~100° C.

In the method, reacting may be performed for 1~24 hr.

The first organic solvent may be one or more selected from the group consisting of methane monochloride, methane dichloride, methane trichloride, methane tetrachloride, ethane dichloride, ethane trichloride, ethane tetrachloride, ethylene dichloride, ethylene trichloride, ethylene tetrachloride, propane dichloride, and propane trichloride.

The second organic solvent or the third organic solvent may be one or more selected from the group consisting of diethyl ether, dichloroethyl ether, diisopropyl ether, n-butyl ether, diisoamyl ether, methylphenyl ether, tetrahydrofuran, ethylene glycol monomethylether, ethylene glycol monoethylether, methyl acetate, ethyl acetate, methyl cellosolve acetate, ethyl cellosolve acetate, diethyl cellosolve acetate, methylethyl carbitol, diethyl carbitol, diethylene glycol monomethylether, diethylene glycol monoethylether, diethylene glycol dimethylether, diethylene glycol methylethylether, diethylene glycol diethylether, propylene glycol methylether acetate, propylene glycol propylether acetate, toluene, xylene, methylethylketone, cyclohexanone, 4-hydroxy-4-methyl-2-pentanone, methyl-n-propylketone, methyl-n-butylketone, methyl-n-amylketone, and 2-heptanone.

The present invention may provide a furfuranol-based compound and a 2-furancarboxylic acid-based compound prepared using the above method.

Advantageous Effects

Therefore, the present invention can provide a method of, in an eco-friendly manner, preparing a furfuranol-based compound and a 2-furancarboxylic acid-based compound using an ionic liquid as a reaction solvent, in which water is not used as the reaction solvent thus preventing the generation of reaction wastewater and also the ionic liquid used as the solvent can be easily recovered and reused.

The present invention can provide a method of profitably preparing a furfuranol-based compound and a 2-furancarboxylic acid-based compound, which has a simple preparation process and a high reaction yield.

The present invention can provide a method of preparing a furfuranol-based compound and a 2-furancarboxylic acid-based compound, which can use a biomass-derived material as a reactant.

MODE FOR INVENTION

Hereinafter, embodiments and examples of the present invention are described in detail so as to be easily performed by a person having ordinary skill in the art.

The following description does not limit the present invention to specific embodiments, and should be understood to include all variations, equivalents or substitutions within the spirit and scope of the present invention. Furthermore, descriptions of known techniques, even if they are pertinent to the present invention, are considered unnecessary and may be omitted in so far as they would make the characteristics of the invention unclear.

The terms used herein are merely intended to explain specific examples and not to limit the present invention. Unless otherwise stated, the singular expression includes a plural expression. In this application, the terms "include" or "have" are used to designate the presence of features, numbers, steps, operations, elements, parts or combinations thereof described in the specification, and should be understood so as not to exclude presence or additional probability of one or more different features, numbers, steps, operations, elements, parts or combinations thereof.

Preparation of Furfuranol-Based Compound and 2-Furancarboxylic Acid-Based Compound As technical means for achieving the technical problem, the present invention provides a method of preparing a furfuranol-based compound and a 2-furancarboxylic acid-based compound, including reacting a furfural-based compound represented by Chemical Formula 1 below with a hydroxide of an alkali metal or an alkaline earth metal using an ionic liquid as a solvent, thus affording a furfuranol-based compound represented by Chemical Formula 2 below and a 2-furancarboxylic acid-based compound represented by Chemical Formula 3 below.

[Chemical Formula 1]

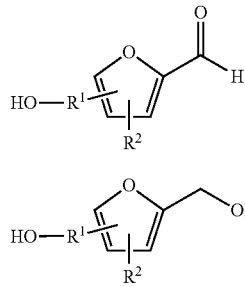

[Chemical Formula 2]

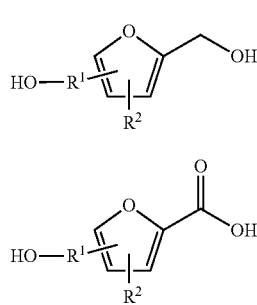

[Chemical Formula 3]

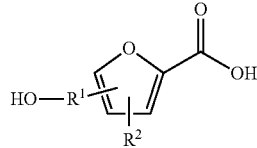

In Chemical Formulas 1 to 3, $R^1$ is independently a valence bond, a $C_{1-10}$ alkylene group, a $C_{3-14}$ cycloalkylene group, a $C_{6-14}$ arylene group, a $C_{6-14}$ alkylarylene group or a $C_{6-14}$ arylalkylene group, and preferably is a valence bond or a $C_{1-3}$ alkylene group, and $R^2$ is independently a hydrogen atom, a $C_{1-10}$ alkyl group, a $C_{3-14}$ cycloalkyl group, a $C_{6-14}$ aryl group, a $C_{6-14}$ alkylaryl group or a $C_{6-14}$ arylalkyl group, and preferably is a hydrogen atom or a $C_{1-3}$ alkyl group.

A reaction used in the present invention is a Cannizzaro reaction. The Cannizzaro reaction is the reaction of 5-hydroxymethylfurfural (HMF) which is a kind of furfural-based compound able to yield both 2,5-dihydroxymethylfuran (DHMF), which is a kind of furfuranol-based compound, and 5-hydroxymethylfuranoic acid (HMFA), which is a kind of 2-furancarboxylic acid-based compound.

In the case of a Cannizzaro reaction using an aqueous solution, reaction efficiency may decrease because of low solubility of the aldehyde used as a starting material in water, and also problems of wastewater treatment may occur due to the use of a large amount of water. Furthermore, HMF is unstable in an aqueous solution and is thus hydrolyzed thus forming byproducts such as levulinic acid and so on. However, the present invention solved the above problems by using, as the reaction solvent, an ionic liquid which is reusable, in lieu of water.

Examples of the ionic liquid usable as the reaction solvent may include an ammonium salt represented by Chemical Formula 4 below, an ammonium salt or phosphonium salt represented by Chemical Formula 5 below, and a sulfonium salt represented by Chemical Formula 6 below, which may be used alone or in mixtures of two or more.

[Chemical Formula 4]

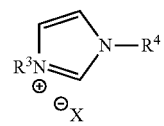

[Chemical Formula 5]

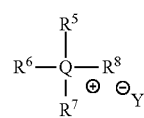

[Chemical Formula 6]

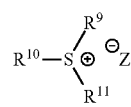

In Chemical Formulas 4 to 6, $R^3$ to $R^{11}$ which are the same as or different from each other are independently a $C_{1-10}$ linear alkyl group, a $C_{3-10}$ branched alkyl group, or a $C_{5-10}$ cycloalkyl group, the main chain or side chain of the $C_{1-10}$ linear alkyl group, $C_{3-10}$ branched alkyl group, or $C_{5-10}$ cycloalkyl group may be unsubstituted or substituted with an oxygen atom, a sulfur atom, a nitrogen atom, a double bond or a triple bond, and Q is a nitrogen atom (N) or a phosphorus atom (P), and X, Y and Z which are the same as or different from each other are independently one or more selected from among $F^-$, $Cl^-$, $Br^-$, $I^-$, $NO_3^-$, $N(CN)_2^-$, $BF_4^-$, $ClO_4^-$, $PF_6^-$, $(CF_3)_2PF_4^-$, $(CF_3)_3PF_3^-$, $(CF_3)_4PF_2^-$, $(CF_3)_5PF^-$, $(CF_3)_6P^-$, $CF_3SO_3^-$, $CF_3CF_2SO_3^-$, $(CF_3SO_2)_2N^-$, $(FSO_2)_2N^-$, $CF_3CF_2(CF_3)_2CO^-$, $(CF_3SO_2)_2CH^-$, $(SF_5)_3C^-$, $(CF_3SO_2)_3C^-$, $CF_3(CF_2)_7SO_3^-$, $CF_3CO_2^-$, $CH_3CO_2^-$, $SCN^-$, and $(CF_3CF_2SO_2)_2N^-$.

Also, examples of the hydroxide of the alkali metal or the alkaline earth metal used in the reaction may include lithium hydroxide, sodium hydroxide, potassium hydroxide, rubidium hydroxide, cesium hydroxide, francium hydroxide, magnesium hydroxide, calcium hydroxide, strontium hydroxide, barium hydroxide and radium hydroxide which may be used alone or in mixtures of two or more.

The amount of the alkali metal or the alkaline earth metal may be 1~30 parts by equivalent based on 1 part by equivalent of the furfural-based compound represented by Chemical Formula 1. If the amount of the alkali metal or the alkaline earth metal is less than 1 part by equivalent, the reaction rate may decrease. In contrast, if the amount thereof is greater than 30 parts by equivalent, it is difficult to separate the furfuranol-based compound and the 2-furancarboxylic acid-based compound from each other via acid-base extraction.

This reaction may be carried out in the temperature range of from 0 to 100° C., and preferably from room temperature to 100° C. If the reaction temperature is lower than 0° C., the reaction proceeds slowly. In contrast, if the reaction temperature is higher than 100° C., the reaction becomes vigorous, undesirably forming large amounts of side-reactions.

The reaction may be carried out for 1~24 hr, and preferably until the starting material is completely reacted.

Although the reaction is typically carried out under atmospheric pressure, it may proceed even under different pressures. The reaction time and temperature may also be properly adjusted depending on changes in the pressure, which will be apparently understood by a person having ordinary skill in the art.

Recovery of Ionic Liquid

After the above reaction, the method of the invention may further include adding a first organic solvent which selectively dissolves the ionic liquid and then performing filtering so that the furfuranol-based compound of Chemical Formula 2 and the 2-furancarboxylic acid-based compound in the metal salt form of Chemical Formula 3 are filtered; and subjecting the first organic solvent to fractional distillation to separate the ionic liquid from the first organic solvent which selectively dissolved the ionic liquid.

Although a variety of kinds of the first organic solvent may be used, the products may mingle together depending on the degree of polarity thereof, and thus particularly useful is an organic solvent which does not dissolve the furfuranol-based compound and the 2-furancarboxylic acid-based compound in metal salt form.

Examples of the first organic solvent may include methane monochloride, methane dichloride, methane trichloride, methane tetrachloride, ethane dichloride, ethane trichloride, ethane tetrachloride, ethylene dichloride, ethylene trichloride, ethylene tetrachloride, propane dichloride, and propane trichloride, which may be used alone or in mixtures of two or more.

In the case where the color of the first organic solvent in which the ionic liquid was dissolved is dark due to impurities, such a solvent may be reused immediately after purification using $Al_2CO_3$ or activated carbon filtering.

Separation of Furfuranol-Based Compound and 2-Furancarboxylic Acid-Based Compound After the above filtering, the method of the invention may further include dissolving the furfuranol-based compound of Chemical Formula 2 and the 2-furancarboxylic acid-based compound in metal salt form of Chemical Formula 3, which were filtered, in water to obtain a compound solution, adjusting the pH of the compound solution to 7~8, adding a second organic solvent thereto, and then performing extraction, thus separating the furfuranol-based compound of Chemical Formula 2; and adjusting the pH of the solution from which the furfuranol-based compound of Chemical Formula 2 was extracted to an acidic range, adding a third organic solvent thereto, and performing extraction, thus separating the 2-furancarboxylic acid-based compound of Chemical Formula 3.

Separating the furfuranol-based compound and the 2-furancarboxylic acid-based compound using acid-base extraction is briefly described below.

The lump of filtered particles obtained upon recovering the ionic liquid is dissolved in a small amount of water, and the second organic solvent is then added thereto, whereby the furfuranol-based compound is primarily extracted. After the completion of the reaction, because the reaction atmosphere is alkaline, neutralization to pH 7~8 using an acid solution is performed so that the extraction is more efficient, followed by conducting the extraction. When the furfuranol-based compound is thoroughly extracted by the second organic solvent, the pH of the remaining aqueous solution is adjusted to be acidic and then the third organic solvent is added thereto, thus extracting the 2-furancarboxylic acid-based compound. This separation is based on different acidities between the furfuranol-based compound and the 2-furancarboxylic acid-based compound.

A variety of kinds of the second organic solvent or the third organic solvent may be used, but an organic solvent having comparatively high polarity may be used because the 2-furancarboxylic acid-based compound does not dissolve well depending on the degree of polarity thereof. The organic solvent usable in the present invention is not an amine and does not mix with water. The amount of the second organic solvent or the third organic solvent used upon acid-base extraction may range from the same as to 500 times the amount of water, and is preferably 50~200 times the amount of water. As such, if the amount of the second organic solvent or the third organic solvent is too small, it is difficult to extract the 2-furancarboxylic acid-based compound having very high polarity.

Specific examples of the second organic solvent or the third organic solvent include but are not limited to diethyl ether, dichloroethyl ether, diisopropyl ether, n-butyl ether, diisoamyl ether, methylphenyl ether, tetrahydrofuran, ethylene glycol monomethylether, ethylene glycol monoethylether, methyl acetate, ethyl acetate, methyl cellosolve acetate, ethyl cellosolve acetate, diethyl cellosolve acetate, methylethyl carbitol, diethyl carbitol, diethylene glycol monomethylether, diethylene glycol monoethylether, diethylene glycol dimethylether, diethylene glycol methylethylether, diethylene glycol diethylether, propylene glycol methylether acetate, propylene glycol propylether acetate, toluene, xylene, methylethylketone, cyclohexanone, 4-hydroxy-4-methyl-2-pentanone, methyl-n-propylketone, methyl-n-butylketone, methyl-n-amylketone, and 2-heptanone, which may be used alone or in combination.

Unless otherwise state, the yield in the present invention is represented by the following Equation 1.

$$\text{Yield (\%)} = (\text{Actual Yield}/\text{Theoretical Yield}) \times 100 \qquad \text{[Equation 1]}$$

The present invention may provide a furfuranol-based compound and a 2-furancarboxylic acid-based compound prepared using the method of the invention as above.

The construction of the present invention is more specifically described via the following examples, but is not limited thereto.

EXAMPLE

The following examples are set to illustrate the present invention but are not construed as limiting the present invention.

Example 1

With reference to Scheme 1 below, 1 ml of 1-ethyl-3-methylimidazolium bis(trifluoromethanesulfonyl)imide ([EMIm]TFSI, available from Merck) newly serving as an ionic liquid was placed in a round-bottom flask, 0.126 g (1 mmol) of 5-hydroxymethylfurfural (HMF, Compound I) was dissolved, the reaction temperature was adjusted to 0° C., and then sodium hydroxide powder (0.200 g, 5 mmol) was added thereto. Subsequently, the reaction temperature was increased to room temperature so that the reaction took place. After completion of the reaction, 20 ml of dichloromethane was added, after which the filtrate obtained via filtration, namely, the dichloromethane layer was distilled under reduced pressure, thus recovering the ionic liquid.

The lump of filtered particles resulting from recovering the ionic liquid was dissolved in 2 ml of water, and then neutralized with 1 N HCl, so that the pH of the solution was adjusted to about 7~8. Extraction using ethyl acetate (3×50 ml) and then concentration under reduced pressure were conducted, yielding 2,5-dihydroxymethylfuran (DHMF, Compound II) as a white solid.

The pH of the remaining water layer was adjusted to about 3, followed by performing extraction using ethyl acetate and then concentration under reduced pressure, yielding 5-hydroxymethylfuranoic acid (HMFA, Compound III) as a light yellow solid. The yields of the products are shown in Table 1 below.

The melting point of the light yellow crystals was 239.5° C., and the light yellow crystals were analyzed to be a target compound using 1H-NMR, 13C-NMR. The analytic data was as follows.

HMFA: 1H NMR (300 MHz, acetone-$d_6$): δ 7.16 (d, J=3.4, 1H), 6.47 (d, J=3.4, 1H), 4.59 (s, 2H); 13C NMR (75 MHz, acetone-$d_6$): δ 160.9, 159.5, 144.9, 119.6, 109.6, 57.3.

DHMF: 1H NMR (300 MHz, acetone-$d_6$): δ 6.18 (s, 2H), 4.48 (d, J=5.8, 4H), 4.18 (t, J=5.8, 2H); 13C NMR (75 MHz, acetone-$d_6$): δ 155.8, 108.22, 57.2.

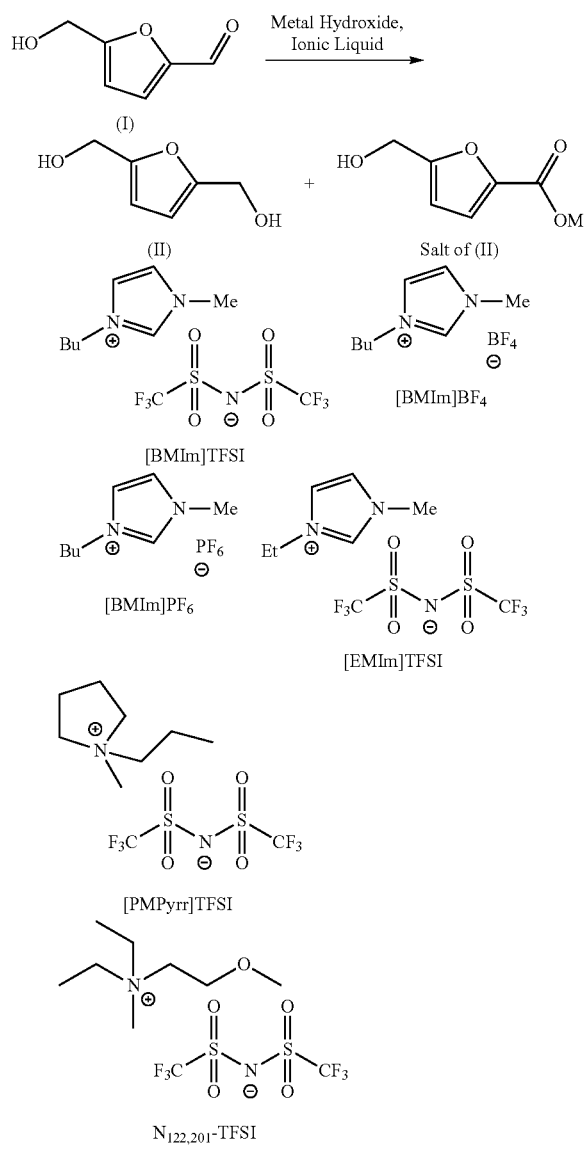

Example 2

DHMF and HMFA were prepared in the same manner as in Example 1, with the exception that 1-butyl-3-methyl imidazolium bis((trifluoromethyl)sulfonyl)imides ([BMIm]TFSI, available from Merck) was used as the ionic liquid instead of 1-ethyl-3-methylimidazolium bis(trifluoromethanesulfonyl) imide ([EMIm]TFSI).

The melting point of the light yellow crystals was 239.5° C., and the light yellow crystals were analyzed to be the target compound using 1H-NMR, 13C-NMR. The analytic data was as follows.

HMFA: 1H NMR (300 MHz, acetone-$d_6$): δ 7.16 (d, J=3.4, 1H), 6.47 (d, J=3.4, 1H), 4.59 (s, 2H); 13C NMR (75 MHz, acetone-$d_6$): δ 160.9, 159.5, 144.9, 119.6, 109.6, 57.3.

DHMF: 1H NMR (300 MHz, acetone-$d_6$): δ 6.18 (s, 2H), 4.48 (d, J=5.8, 4H), 4.18 (t, J=5.8, 2H); 13C NMR (75 MHz, acetone-$d_6$): δ 155.8, 108.22, 57.2.

Example 3

DHMF and HMFA were prepared in the same manner as in Example 1, with the exception that 1-methyl-1-propylpyrrolidinium bis(trifluoromethanesulfonyl)imide ([PMPyrr] TFSI, available from Sigma-aldrich) was used as the ionic liquid instead of 1-ethyl-3-methylimidazolium bis(trifluoromethanesulfonyl)imide ([EMIm]TFSI).

The melting point of the light yellow crystals was 239.5° C., and the light yellow crystals were analyzed to be the target compound using 1H-NMR, 13C-NMR. The analytic data was as follows.

HMFA: 1H NMR (300 MHz, acetone-$d_6$): δ 7.16 (d, J=3.4, 1H), 6.47 (d, J=3.4, 1H), 4.59 (s, 2H); 13C NMR (75 MHz, acetone-$d_6$): δ 160.9, 159.5, 144.9, 119.6, 109.6, 57.3.

DHMF: 1H NMR (300 MHz, acetone-$d_6$): δ 6.18 (s, 2H), 4.48 (d, J=5.8, 4H), 4.18 (t, J=5.8, 2H); 13C NMR (75 MHz, acetone-$d_6$): δ 155.8, 108.22, 57.2.

Example 4

DHMF and HMFA were prepared in the same manner as in Example 1, with the exception that N,N-diethyl-N-methyl-N-(2-methoxyethyl)ammonium bis(trifluoromethylsulfonyl) imide ($N_{122,201}$-TFSI, available from Sigma-aldrich) was used as the ionic liquid instead of 1-ethyl-3-methylimidazolium bis(trifluoromethanesulfonyl)imide ([EMIm]TFSI).

The melting point of the light yellow crystals was 239.5° C., and the light yellow crystals were analyzed to be the target compound using 1H-NMR, 13C-NMR. The analytic data was as follows.

HMFA: 1H NMR (300 MHz, acetone-$d_6$): δ 7.16 (d, J=3.4, 1H), 6.47 (d, J=3.4, 1H), 4.59 (s, 2H); 13C NMR (75 MHz, acetone-$d_6$): δ 160.9, 159.5, 144.9, 119.6, 109.6, 57.3.

DHMF: 1H NMR (300 MHz, acetone-$d_6$): δ 6.18 (s, 2H), 4.48 (d, J=5.8, 4H), 4.18 (t, J=5.8, 2H); 13C NMR (75 MHz, acetone-$d_6$): δ 155.8, 108.22, 57.2.

Example 5

DHMF and HMFA were prepared in the same manner as in Example 1, with the exception that 1-butyl-3-methylimidazolium tetrafluoroborate ([BMIm]$BF_4$, available from C-TRI) was used as the ionic liquid instead of 1-ethyl-3-methylimidazolium bis(trifluoromethanesulfonyl)imide ([EMIm]TFSI).

The melting point of the light yellow crystals was 239.5° C., and the light yellow crystals were analyzed to be the target compound using 1H-NMR, 13C-NMR. The analytic data was as follows.

HMFA: 1H NMR (300 MHz, acetone-$d_6$): δ 7.16 (d, J=3.4, 1H), 6.47 (d, J=3.4, 1H), 4.59 (s, 2H); 13C NMR (75 MHz, acetone-$d_6$): δ 160.9, 159.5, 144.9, 119.6, 109.6, 57.3.

DHMF: 1H NMR (300 MHz, acetone-$d_6$): δ 6.18 (s, 2H), 4.48 (d, J=5.8, 4H), 4.18 (t, J=5.8, 2H); 13C NMR (75 MHz, acetone-$d_6$): δ 155.8, 108.22, 57.2.

Example 6

DHMF and HMFA were prepared in the same manner as in Example 1, with the exception that 1-butyl-3-methyl imidazolium hexafluorophosphate ([BMIm]$PF_6$, available from C-TRI) was used as the ionic liquid instead of 1-ethyl-3-methylimidazolium bis(trifluoromethanesulfonyl)imide ([EMIm]TFSI).

The melting point of the light yellow crystals was 239.5° C., and the light yellow crystals were analyzed to be the target compound using 1H-NMR, 13C-NMR. The analytic data was as follows.

HMFA: 1H NMR (300 MHz, acetone-$d_6$): δ 7.16 (d, J=3.4, 1H), 6.47 (d, J=3.4, 1H), 4.59 (s, 2H); 13C NMR (75 MHz, acetone-$d_6$): δ 160.9, 159.5, 144.9, 119.6, 109.6, 57.3.

DHMF: 1H NMR (300 MHz, acetone-$d_6$): δ 6.18 (s, 2H), 4.48 (d, J=5.8, 4H), 4.18 (t, J=5.8, 2H); 13C NMR (75 MHz, acetone-$d_6$): δ 155.8, 108.22, 57.2.

Example 7

DHMF and HMFA were prepared in the same manner as in Example 1, with the exception that potassium hydroxide (KOH) was used instead of sodium hydroxide (NaOH).

The melting point of the light yellow crystals was 239.5° C., and the light yellow crystals were analyzed to be the target compound using 1H-NMR, 13C-NMR. The analytic data was as follows.

HMFA: 1H NMR (300 MHz, acetone-$d_6$): δ 7.16 (d, J=3.4, 1H), 6.47 (d, J=3.4, 1H), 4.59 (s, 2H); 13C NMR (75 MHz, acetone-$d_6$): δ 160.9, 159.5, 144.9, 119.6, 109.6, 57.3.

DHMF: 1H NMR (300 MHz, acetone-$d_6$): δ 6.18 (s, 2H), 4.48 (d, J=5.8, 4H), 4.18 (t, J=5.8, 2H); 13C NMR (75 MHz, acetone-$d_6$): δ 155.8, 108.22, 57.2.

Example 8

DHMF and HMFA were prepared in the same manner as in Example 1, with the exception that cesium hydroxide (CsOH) was used instead of sodium hydroxide (NaOH).

The melting point of the light yellow crystals was 239.5° C., and the light yellow crystals were analyzed to be the target compound using 1H-NMR, 13C-NMR. The analytic data was as follows.

HMFA: 1H NMR (300 MHz, acetone-$d_6$): δ 7.16 (d, J=3.4, 1H), 6.47 (d, J=3.4, 1H), 4.59 (s, 2H); 13C NMR (75 MHz, acetone-$d_6$): δ 160.9, 159.5, 144.9, 119.6, 109.6, 57.3.

DHMF: 1H NMR (300 MHz, acetone-$d_6$): δ 6.18 (s, 2H), 4.48 (d, J=5.8, 4H), 4.18 (t, J=5.8, 2H); 13C NMR (75 MHz, acetone-$d_6$): δ 155.8, 108.22, 57.2.

Example 9

DHMF and HMFA were prepared in the same manner as in Example 1, with the exception that barium hydroxide (Ba(OH)$_2$) was used instead of sodium hydroxide (NaOH).

The melting point of the light yellow crystals was 239.5° C., and the light yellow crystals were analyzed to be the target compound using 1H-NMR, 13C-NMR. The analytic data was as follows.

HMFA: 1H NMR (300 MHz, acetone-$d_6$): δ 7.16 (d, J=3.4, 1H), 6.47 (d, J=3.4, 1H), 4.59 (s, 2H); 13C NMR (75 MHz, acetone-$d_6$): δ 160.9, 159.5, 144.9, 119.6, 109.6, 57.3.

DHMF: 1H NMR (300 MHz, acetone-$d_6$): δ 6.18 (s, 2H), 4.48 (d, J=5.8, 4H), 4.18 (t, J=5.8, 2H); 13C NMR (75 MHz, acetone-$d_6$): δ 155.8, 108.22, 57.2.

Example 10

This example was conducted in the same manner as in Example 1, with the exception that 1-ethyl-3-methylimidazolium bis(trifluoromethanesulfonyl)imide [EMIm]TFSI recovered in Example 1 was used as the reaction solvent instead of 1-ethyl-3-methylimidazolium bis(trifluoromethanesulfonyl)imide [EMIm]TFSI newly used in Example 1.

Example 11

This example was conducted in the same manner as in Example 1, with the exception that 1-ethyl-3-methylimidazolium bis(trifluoromethanesulfonyl)imide [EMIm]TFSI recovered in Example 10 was used as the reaction solvent instead of 1-ethyl-3-methylimidazolium bis(trifluoromethanesulfonyl)imide [EMIm]TFSI newly used in Example 1.

Example 12

This example was conducted in the same manner as in Example 1, with the exception that 1-ethyl-3-methylimidazolium bis(trifluoromethanesulfonyl)imide [EMIm]TFSI recovered in Example 11 was used as the reaction solvent instead of 1-ethyl-3-methylimidazolium bis(trifluoromethanesulfonyl)imide [EMIm]TFSI newly used in Example 1.

Example 13

This example was conducted in the same manner as in Example 1, with the exception that 1-ethyl-3-methylimidazolium bis(trifluoromethanesulfonyl)imide [EMIm]TFSI recovered in Example 12 was used as the reaction solvent instead of 1-ethyl-3-methylimidazolium bis(trifluoromethanesulfonyl)imide [EMIm]TFSI newly used in Example 1.

Nuclear Magnetic Resonance

Nuclear magnetic resonance was measured using JNM-LA300 (1H-300 MHz, 13 C-75 MHz) available from JEOL in the crystals of respective examples dissolved in deuterated acetone (acetone-$d_6$) containing 0.05% tetramethylsilane (TMS) as an internal standard material.

TABLE 1

| Ex. | Ionic Liquid | Base | Reused Frequency of Ionic Liquid | DHMF Yield (%) | HMFA Yield (%) |
|---|---|---|---|---|---|
| 1 | [EMIm]TFSI | NaOH | 0 | 100 | 84 |
| 2 | [BMIm]TFSI | NaOH | 0 | 84 | 88 |
| 3 | [PMPyrr]TFSI | NaOH | 0 | 84 | 74 |
| 4 | $N_{122,201}$—TFSI | NaOH | 0 | 88 | 76 |
| 5 | [BMIm]$BF_4$ | NaOH | 0 | 26 | 34 |
| 6 | [BMIm]$PF_6$ | NaOH | 0 | 28 | 22 |
| 7 | [EMIm]TFSI | KOH | 0 | 80 | 70 |
| 8 | [EMIm]TFSI | CsOH | 0 | 64 | 56 |
| 9 | [EMIm]TFSI | Ba(OH)$_2$ | 0 | 54 | 22 |
| 10 | [EMIm]TFSI | NaOH | 1 | 92 | 92 |
| 11 | [EMIm]TFSI | NaOH | 2 | 86 | 90 |
| 12 | [EMIm]TFSI | NaOH | 3 | 82 | 84 |
| 13 | [EMIm]TFSI | NaOH | 4 | 90 | 92 |

As described hereinbefore, both DHMF and HMFA which are high value-added can be obtained at high yield thanks to the Cannizzaro reaction of the invention. This is considered to be because an ionic liquid is used as the reaction solvent, thus preventing hydrolysis of a starting material which is regarded as the main cause of low yield and also more effectively separating DHMF and HMFA which are not easy to separate due to high solubility in water. Moreover, reaction wastewater resulting from conventional aqueous solution reactions is not formed, and the method of the invention is much more profitable and eco-friendly thanks to the reuse of the ionic liquid, compared to conventional processes. Also, the products can be simply and efficiently separated, and high reaction efficiency and superior productivity can be attained owing to the use of metal hydroxide powder.

Although the embodiments of the present invention have been disclosed for illustrative purposes, those skilled in the art will appreciate that diverse variations and modifications are possible, without departing from the spirit and scope of the invention. Thus, the above embodiments should be understood not to be limited but to be illustrated. For example, respective elements described in an integrated form may be dividedly used, and the divided elements may be used in a state of being combined.

The scope of the present invention is defined by, rather than the above detailed description, the claims which will be described later, and all variations or modifications deduced from the meanings, scope and equivalents of the claims are intended to be included in the scope of the present invention.

INDUSTRIAL APPLICABILITY

The present invention can provide a method of, in an eco-friendly manner, preparing a furfuranol-based compound and a 2-furancarboxylic acid-based compound using an ionic liquid as a reaction solvent, in which water is not used as the reaction solvent, thus preventing the generation of reaction wastewater, and the ionic liquid used as the solvent can be easily recovered and reused.

The present invention can provide a method of profitably preparing a furfuranol-based compound and a 2-furancarboxylic acid-based compound, which has a simple preparation process and a high reaction yield.

The present invention can provide a method of preparing a furfuranol-based compound and a 2-furancarboxylic acid-based compound, in which a biomass-derived material can be used as a reactant.

The invention claimed is:

1. A method of preparing a furfuranol-based compound and a 2-furancarboxylic acid-based compound, comprising:
reacting a furfural-based compound represented by Chemical Formula 1 below with a hydroxide of an alkali metal or an alkaline earth metal using an ionic liquid as a solvent, thus obtaining a furfuranol-based compound represented by Chemical Formula 2 below and a 2-furancarboxylic acid-based compound represented by Chemical Formula 3 below,

[Chemical Formula 1]

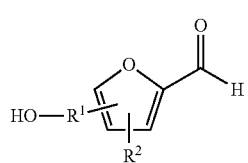

[Chemical Formula 2]

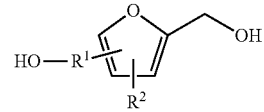

[Chemical Formula 3]

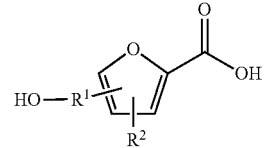

wherein,
$R^1$ is independently a valence bond, a $C_{1-10}$ alkylene group, a $C_{3-14}$ cycloalkylene group, a $C_{6-14}$ arylene group, a $C_{6-14}$ alkylarylene group or a $C_{6-14}$ arylalkylene group, and
$R^2$ is independently a hydrogen atom, a $C_{1-10}$ alkyl group, a $C_{3-14}$ cycloalkyl group, a $C_{6-14}$ aryl group, a $C_{6-14}$ alkylaryl group or a $C_{6-14}$ arylalkyl group.

2. The method of claim 1, wherein $R^1$ is independently a valence bond or a $C_{1-3}$ alkylene group, and $R^2$ is independently a hydrogen atom or a $C_{1-3}$ alkyl group.

3. The method of claim 1, further comprising, after the reacting:
adding a first organic solvent which selectively dissolves the ionic liquid and then performing filtering so that the furfuranol-based compound of Chemical Formula 2 and the 2-furancarboxylic acid-based compound in metal salt form of Chemical Formula 3 are filtered; and
subjecting the first organic solvent to fractional distillation to separate the ionic liquid from the first organic solvent which selectively dissolved the ionic liquid.

4. The method of claim 3, further comprising, after the filtering:
dissolving the furfuranol-based compound of Chemical Formula 2 and the 2-furancarboxylic acid-based compound in metal salt form of Chemical Formula 3, which were filtered, in water to obtain a compound solution, adjusting a pH of the compound solution to 7~8, adding a second organic solvent thereto, and then performing extraction, thus separating the furfuranol-based compound of Chemical Formula 2; and
adjusting a pH of the solution from which the furfuranol-based compound of Chemical Formula 2 was extracted to an acidic range, adding a third organic solvent thereto, and then performing extraction, thus separating the 2-furancarboxylic acid-based compound of Chemical Formula 3.

5. The method of claim 1, wherein the ionic liquid is one or more selected from the group consisting of an ammonium salt represented by Chemical Formula 4 below, an ammonium salt or phosphonium salt represented by Chemical Formula 5 below, and a sulfonium salt represented by Chemical Formula 6 below,

[Chemical Formula 4]

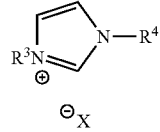

-continued

[Chemical Formula 5]

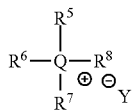

[Chemical Formula 6]

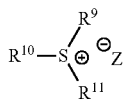

wherein,

R$^3$ to R$^{11}$ which are same as or different from each other are independently a C$_{1-10}$ linear alkyl group, a C$_{3-10}$ branched alkyl group, or a C$_{5-10}$ cycloalkyl group, a main chain or side chain of the C$_{1-10}$ linear alkyl group, C$_{3-10}$ branched alkyl group, or C$_{5-10}$ cycloalkyl group being unsubstituted or substituted with an oxygen atom, a sulfur atom, a nitrogen atom, a double bond or a triple bond;

Q is a nitrogen atom (N) or a phosphorus atom (P); and

X, Y and Z which are same as or different from each other are independently one or more selected from among F$^-$, Cl$^-$, Br$^-$, I$^-$, NO$_3^-$, N(CN)$_2^-$, BF$_4^-$, ClO$_4^-$, PF$_6^-$, (CF$_3$)$_2$PF$_4^-$, (CF$_3$)$_3$PF$_3^-$, (CF$_3$)$_4$PF$_2^-$, (CF$_3$)$_5$PF$^-$, (CF$_3$)$_6$P$^-$, CF$_3$SO$_3^-$, CF$_3$CF$_2$SO$_3^-$, (CF$_3$SO$_2$)$_2$N$^-$, (FSO$_2$)$_2$N$^-$, CF$_3$CF$_2$(CF$_3$)$_2$CO$^-$, (CF$_3$SO$_2$)$_2$CH$^-$, (SF$_5$)$_3$C$^-$, (CF$_3$SO$_2$)$_3$C$^-$, CF$_3$(CF$_2$)$_7$SO$_3^-$, CF$_3$CO$_2^-$, CH$_3$CO$_2^-$, SCN$^-$, and (CF$_3$CF$_2$SO$_2$)$_2$N$^-$.

6. The method of claim 1, wherein the hydroxide of the alkali metal or the alkaline earth metal is one or more selected from the group consisting of lithium hydroxide, sodium hydroxide, potassium hydroxide, rubidium hydroxide, cesium hydroxide, francium hydroxide, magnesium hydroxide, calcium hydroxide, strontium hydroxide, barium hydroxide and radium hydroxide.

7. The method of claim 1, wherein the alkali metal or the alkaline earth metal is used in an amount of 1-30 parts by equivalent based on 1 part by equivalent of the furfural-based compound represented by Chemical Formula 1.

8. The method of claim 1, wherein the reacting is performed at 0-100° C.

9. The method of claim 1, wherein the reacting is performed for 1-24 hr.

10. The method of claim 3, wherein the first organic solvent is one or more selected from the group consisting of methane monochloride, methane dichloride, methane trichloride, methane tetrachloride, ethane dichloride, ethane trichloride, ethane tetrachloride, ethylene dichloride, ethylene trichloride, ethylene tetrachloride, propane dichloride, and propane trichloride.

11. The method of claim 4, wherein the second organic solvent or the third organic solvent is one or more selected from the group consisting of diethyl ether, dichloroethyl ether, diisopropyl ether, n-butyl ether, diisoamyl ether, methylphenyl ether, tetrahydrofuran, ethylene glycol monomethylether, ethylene glycol monoethylether, methyl acetate, ethyl acetate, methyl cellosolve acetate, ethyl cellosolve acetate, diethyl cellosolve acetate, methylethyl carbitol, diethyl carbitol, diethylene glycol monomethylether, diethylene glycol monoethylether, diethylene glycol dimethylether, diethylene glycol methylethylether, diethylene glycol diethylether, propylene glycol methylether acetate, propylene glycol propylether acetate, toluene, xylene, methylethylketone, cyclohexanone, 4-hydroxy-4-methyl-2-pentanone, methyl-n-propylketone, methyl-n-butylketone, methyl-n-amylketone, and 2-heptanone.

* * * * *